United States Patent
Flower et al.

[11] Patent Number: 5,873,850
[45] Date of Patent: Feb. 23, 1999

[54] LOCKING AND DISFIGURING MECHANISM FOR AN IONTOPHORETIC SYSTEM

[75] Inventors: Ronald J. Flower, Lawrenceville, Ga.; Charles M. Huck, Somerville, N.J.

[73] Assignee: Becton Dickinson and Company, Franklin Lakes, N.J.

[21] Appl. No.: 864,951

[22] Filed: May 29, 1997

[51] Int. Cl.⁶ .................................................. A61N 1/30
[52] U.S. Cl. ........................... 604/20; 607/152; 439/475
[58] Field of Search .............................. 604/20; 439/301, 439/163, 475, 592, 260, 387; 607/152

[56] References Cited

U.S. PATENT DOCUMENTS

| | | |
|---|---|---|
| 4,702,256 | 10/1987 | Robinson et al. . |
| 5,160,316 | 11/1992 | Henley . |
| 5,458,569 | 10/1995 | Kirk, III et al. . |
| 5,498,235 | 3/1996 | Flower . |

*Primary Examiner*—Mark Bockelman
*Attorney, Agent, or Firm*—Allen W. Wark; David T. Banchik

[57] ABSTRACT

An iontophoretic system including a controller and a patch is provided. The controller has a receiving portion including an upper surface and a lower surface, and a member protruding from the lower surface in a ramp-like fashion toward the upper surface and terminating in a top edge near the upper surface. The patch has an interconnection tab including an opening for engaging the protruding member of the controller when the interconnection tab is inserted into the receiving portion of the controller and the opening falls over the top edge of the protruding member.

11 Claims, 7 Drawing Sheets

5,873,850

LOCKING AND DISFIGURING MECHANISM FOR AN IONTOPHORETIC SYSTEM

BACKGROUND OF THE INVENTION

1. Field of the Invention

The invention relates to a locking and disfiguring mechanism for an iontophoretic system including a patch and a controller.

2. Description of Related Art

Iontophoresis is the migration of ions when an electrical current is passed through a solution containing an ionized species, usually the ionic form of a drug or other therapeutic agent (hereinafter referred to as the "drug"). One particularly advantageous application of iontophoresis is the noninvasive transdermal delivery of ionized drugs into a patient. Iontophoretic drug delivery offers an alternative and effective method of drug delivery over other methods such as passive transdermal patches, needle injection, and oral ingestion, and is an especially effective method for children, the bedridden and the elderly.

Drug delivery via iontophoresis is done by applying current to electrodes of an iontophoretic patch. The current is usually supplied from a controller connected to the patch. The electrodes are respectively arranged within a drug reservoir, containing the drug ions, and a return reservoir, containing an electrolyte. When the patch is placed on the skin of a patient and the controller is turned on, the current applied to the electrodes forces the drug ions contained in the drug reservoir through the patient's skin and into the patient's bloodstream.

The controller usually contains an energy source, for example, a battery, as well as electrical circuitry for generating and regulating the current applied to the patch electrodes. Preferably, the controller is to be reused until its battery dies, while the patch is to be used only once to deliver a full drug dosage and then disposed.

The controller and patch may be connected together via an interconnection tab integral to the patch. This connection is (1) electrical—electrical interconnect leads and terminals connect the electrodes to the current regulating circuitry; and (2) mechanical—the tab is physically engaged in the controller housing. A problem in this connection may arise, however, if the interconnection tab can be easily removed from the controller housing during operation of the system. This will cause the patch to separate, either wholly or partially, from the controller, which in turn causes the patch to disconnect electrically from the controller. Without an electrical connection, drug delivery to the patient will cease, and the patient will receive only a partial drug dosage.

Another problem that may arise is the reuse, by the patient or health care provider, of a partially-used or spent patch. This reuse may be accidental or may be purposeful, but should be avoided. Not only is reusing a patch unsanitary, but will most likely result in the delivery of only a partial drug dosage.

SUMMARY OF THE INVENTION

The present invention advantageously provides a locking mechanism to ensure, the mechanical and electrical connection between a patch and a controller.

The present invention also advantageously provides means for feeding back to the user an increasing tactile resistance when the patch is inserted into the controller, and a mild "snap" when the patch is fully engaged.

The present invention also advantageously provides a mechanism for disfiguring or deforming the patch upon its removal from the controller to prevent its subsequent reuse by the patient or health care provider.

In one aspect of the present invention, an iontophoretic system is provided including a controller and a patch. The controller includes a portion for receiving the patch. This receiving portion has a protruding member which ramps from the front lower surface of the receiving portion, towards the rear of the receiving portion, so that its top edge is near the upper surface of the receiving portion. The patch includes an interconnection tab having an opening. When the interconnection tab is inserted into the receiving portion of the controller, the opening rises over the top edge of the protruding member and engages the protruding member, thus locking the patch to the controller.

In another aspect of the present invention, a method for rendering a patch unreusable is provided. An interconnection tab of the patch is inserted into a controller so that the opening of the interconnection tab engages a protruding member of a receiving portion of the controller. When the patch is removed from the receiving portion of the controller, either by squeezing and pulling the patch or by pulling the patch against a cutting edge of the protruding member, the interconnection tab is permanently disfigured. This prevents its re-engagement onto the protruding member of the controller, thus preventing its reuse.

BRIEF DESCRIPTION OF THE DRAWINGS

These and other features and advantages of the present invention can best be understood by reference to the detailed description of the preferred embodiments set forth below taken in conjunction with the drawings, in which.

DETAILED DESCRIPTION OF THE PREFERRED EMBODIMENTS

Figure 1:
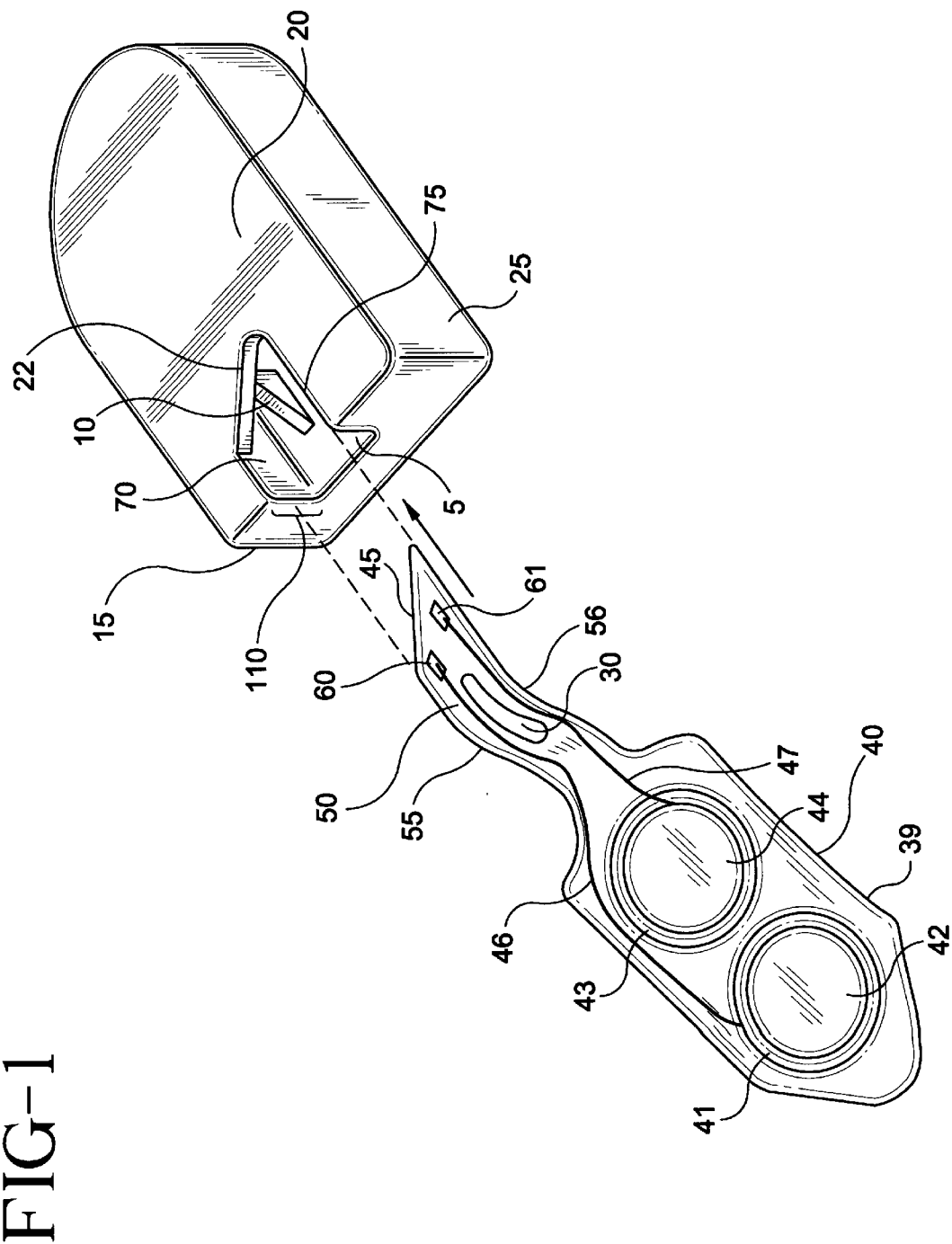
FIG. 1 is a perspective view of an iontophoretic system illustrating a first embodiment of the present invention.
Figure 2:
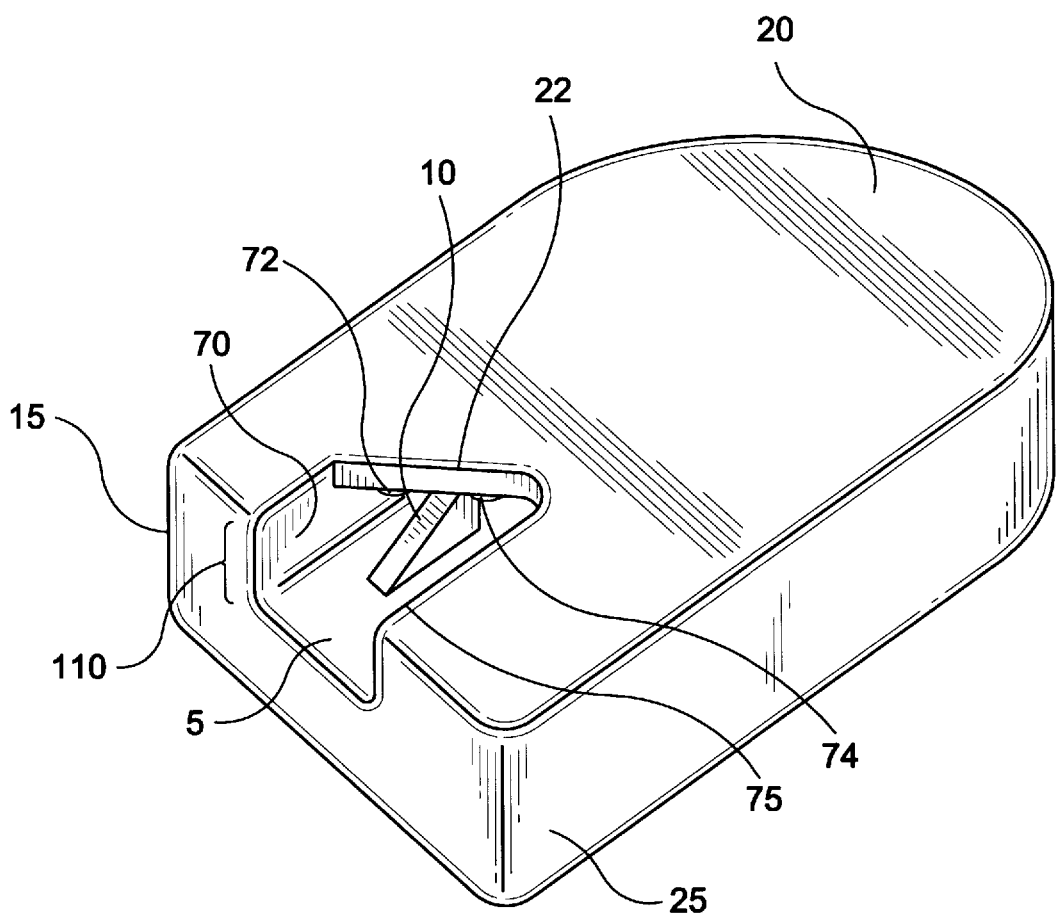
FIG. 2 is a perspective view of a controller illustrating the second embodiment of the present invention.
Figure 3A:
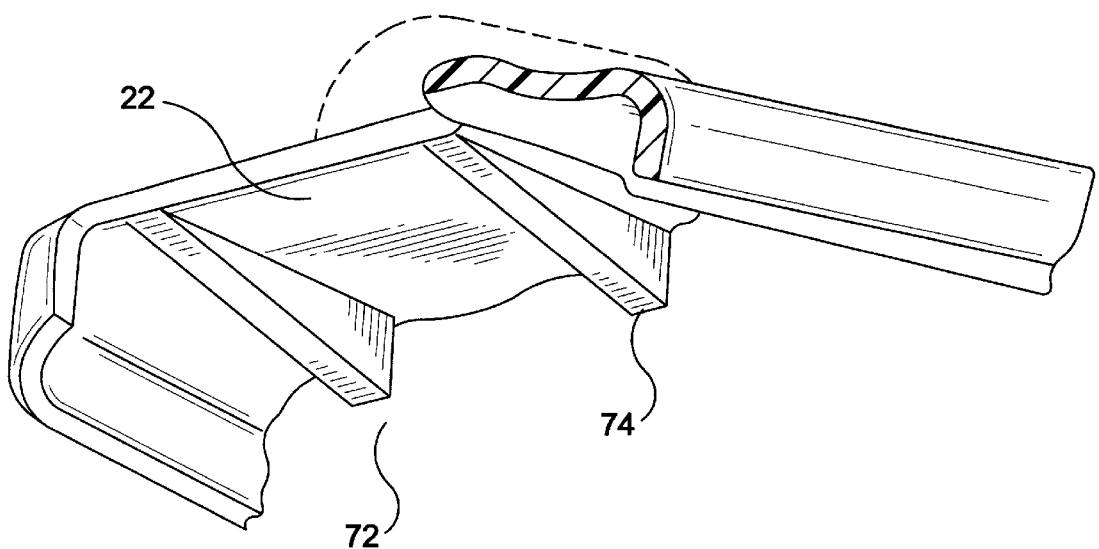
FIG. 3A is a sectional view of the upper surface of the receiving portion of a controller illustrating the second embodiment of the present invention.
Figure 3B:
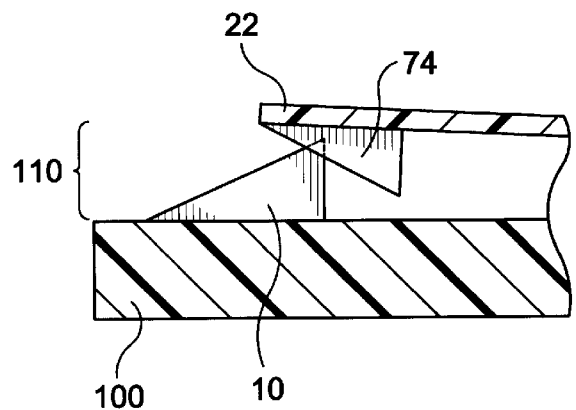
FIG. 3B is a sectional view of the receiving portion of a controller illustrating the second embodiment of the present invention.

The first embodiment of the present invention relates to an iontophoretic system including a patch 40 and a controller 20, as illustrated in FIG. 1. The controller 20 includes an outer casing which houses the energy source and current regulation circuitry required for driving current into the patch 40. The casing of the controller 20 may be made of a plastic, metal or other suitable material for encasing and protecting the current regulating circuitry.

In the first embodiment, the controller 20 includes a receiving portion 110, located substantially in the front and center of the controller 20, between a first edge 15 and a second edge 25 of the controller 20. The location of the receiving portion 110 in the controller 20 is not limited, however, to the front and center and may be located at other positions about the controller 20. The controller 20 includes a lower protruding member 10, which is located substantially in the center of the receiving portion 110 between a first side 70 and a second side 75 of the receiving portion 110, and arises from a lower surface 5 of the receiving portion 110. The controller 20 may also include one or more upper protruding members descending from an upper surface 22 of the receiving portion 110, which will be described in more detail below in connection with a second embodiment. The location of the lower protruding member 10 is not limited to the center of the receiving portion 110 and may be located at other positions within the receiving portion 110.

The lower protruding member 10 may slant angularly, in a ramping fashion, so as to rise from the lower surface 5 and terminate near the upper surface 22 of the receiving portion 110. This configuration of the lower protruding member 10 within receiving portion 110 advantageously feeds back to the user an increasing tactile resistance when the user inserts the patch 40 into the receiving portion 110, as described in more detail below.

The patch 40 includes an active reservoir 41, usually containing drug ions in a gel, and a return reservoir 43, usually containing an electrolytic gel, into which are placed the anode 42 and cathode 44. The placement of the anode 42 or the cathode 44 into the active reservoir depends on the polarity of the drug ions, as is known in the iontophoretic art. Electrical interconnectors, such as wires or circuit traces 46 and 47, respectively connect the anode 42 and cathode 44 to the current source of the controller, through terminals 60 and 61, when the patch is inserted into the controller.

The patch 40 also includes a backing layer 39 and an interconnection tab 50. The backing layer 39 and tab 50 are made of a sturdy, dielectric, flexible material such as plastic or the like. This material may also be permanently deformable. The tab 50 has an opening 30, such as a narrow slot, for engaging the lower protruding member 10 of the receiving portion 110 when patch 40 is inserted into the controller 20. The opening 30 may be formed in any number of different shapes including, but not limited to, oval, circular, triangular or square shapes, so long as the opening 30 engages onto the lower protruding member 10 when the patch is inserted into the controller, and the patch is held securely into place with a minimum of movement thereafter.

The patch 40 is connected to the controller 20 by inserting the interconnection tab 50 into the receiving portion 110 of the controller 20. As an end portion 45 of the interconnection tab 50 slides over the lower protruding member 10, resistance to insertion of the tab 50 of the patch 40 increases, thus providing tactile feedback to the user. A mild "snap" is also preferably felt by the user as the opening 30 fully engages and locks onto the lower protruding member 10.

This arrangement relies on the natural resilience of the patch tab material to act as a spring as long as the material is not overstressed. When the patch is removed, the patch tab material becomes overstressed and the patch tab is deformed permanently, such that the opening 30 can no longer securely engage the lower protruding member 10 upon reinsertion of the patch into the controller, thus preventing reuse of the patch after removal, as described in more detail below.

Moreover, this arrangement firmly locks the patch 40 into the receiving portion 110 of the controller 20, ensuring that the patch 40 cannot be easily removed from the controller 20 through inadvertence by a slight pulling of the interconnection tab 50, thereby providing a secure mechanical and electrical connection. This feature also advantageously prevents the inadvertent insertion of a patch into the controller 20.

In a second embodiment of the present invention, illustrated in FIGS. 2, 3A–B and 5B, an upper protruding member, located on one side or the other of the lower protruding member 10, is provided. The upper protruding member may slant angularly, in a ramping fashion, so as to descend downwardly from the upper surface 22 of the receiving portion 110. As shown in these figures, two upper protruding members 72 and 74 are provided, one on each side of the lower protruding member 10. The addition of these upper protruding members to the receiving portion 110 greatly enhances the tactile feedback and "snap" felt by the user when inserting tab 50 of the patch 40 into receiving portion 110 of the controller 20.

Figure 4:
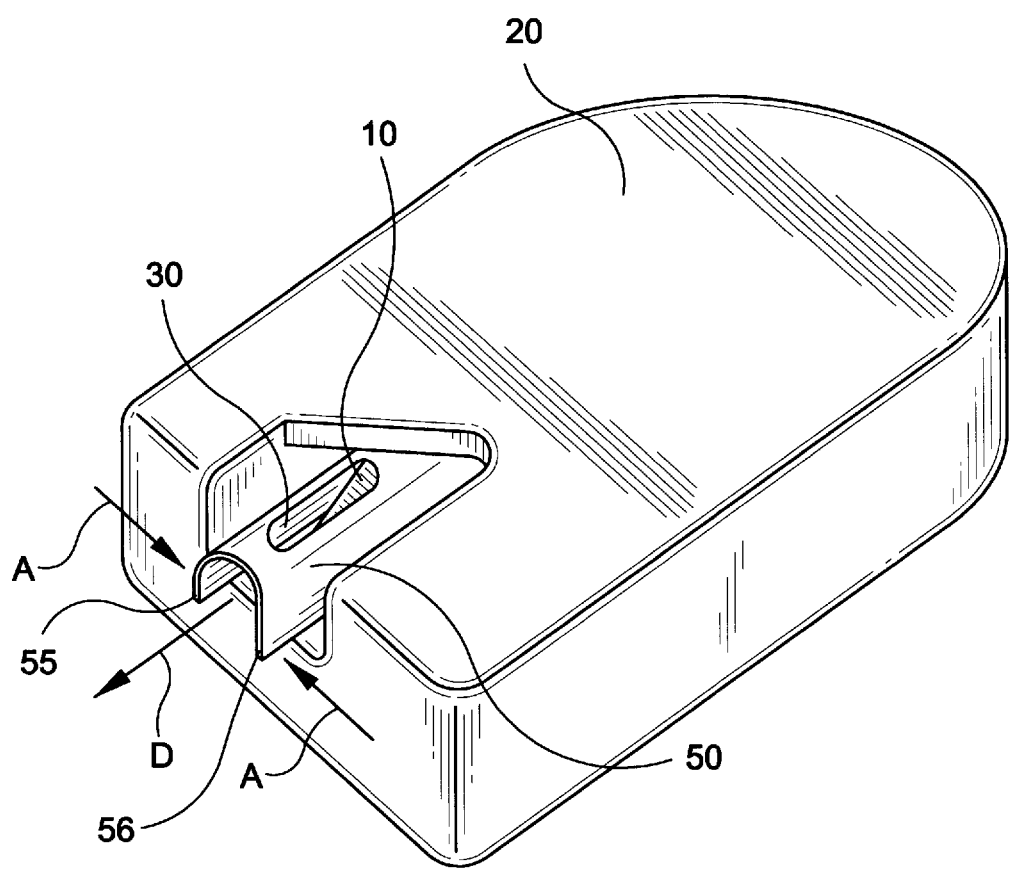
FIG. 4 is a perspective view of a controller illustrating the third embodiment of the present invention.
Figure 5A:
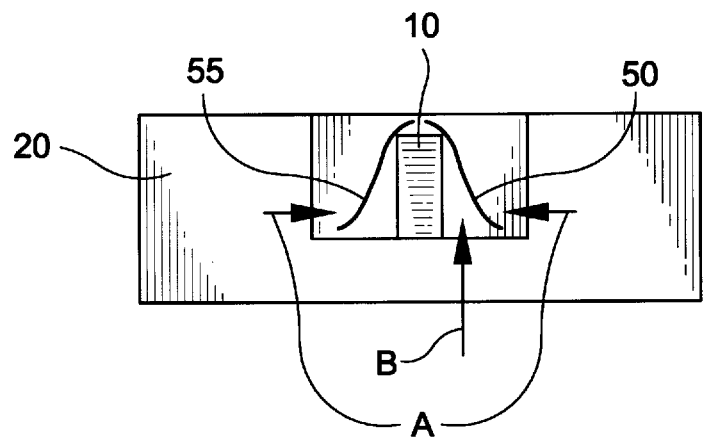
FIG. 5A is an end view of the controller of the first embodiment of the present invention.
Figure 5B:
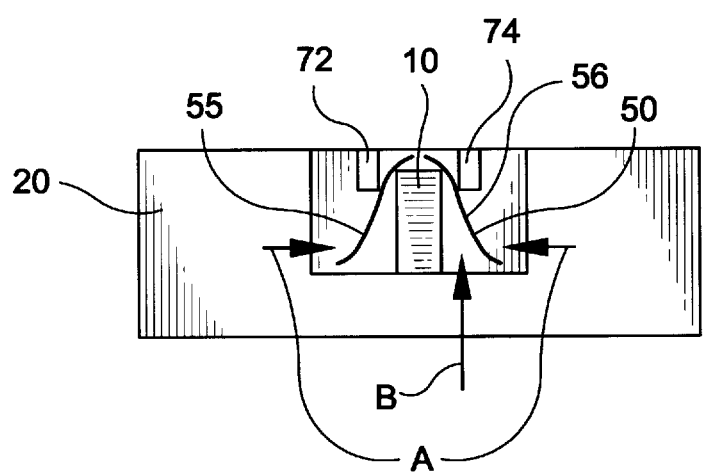
FIG. 5B is an end view of the controller of the second embodiment of the present invention.

In a third embodiment of the present invention, the patch 40 is removed from the receiving portion 110 of the controller 20 by squeezing sides 55 and 56 of the tab 50 toward each other. In this embodiment, the tab is preferably made of a material that permanently deforms when squeezed. As illustrated in FIGS. 4 and 5A–B, the inward force of the squeezing motion, depicted by arrows A, causes the tab 50 to bulge upwardly (toward direction B) in its center, allowing the opening 30 to rise up above and disengage the protruding member 10 (to illustrate the squeezing action more clearly, only a cut-away of the inserted portion of tab 50 is shown in the FIG. 6.

At that time, the tab 50 is then pulled outwardly, in the direction indicated by arrow D, from the receiving portion 110, resulting in the electrical and mechanical disconnection of the patch 40 from the controller 20. The action of squeezing together sides 55 and 56 of the tab 50 deforms the tab material so as to disfigure permanently the tab 50 into the shape as shown by the cross-section in FIG. 4. This disfigurement prevents the patch 40 from reconnecting to the controller 20 because the disfigured tab 50 cannot interlock with the protruding member 10. Thus, the use of the patch is prevented.

Figure 6:
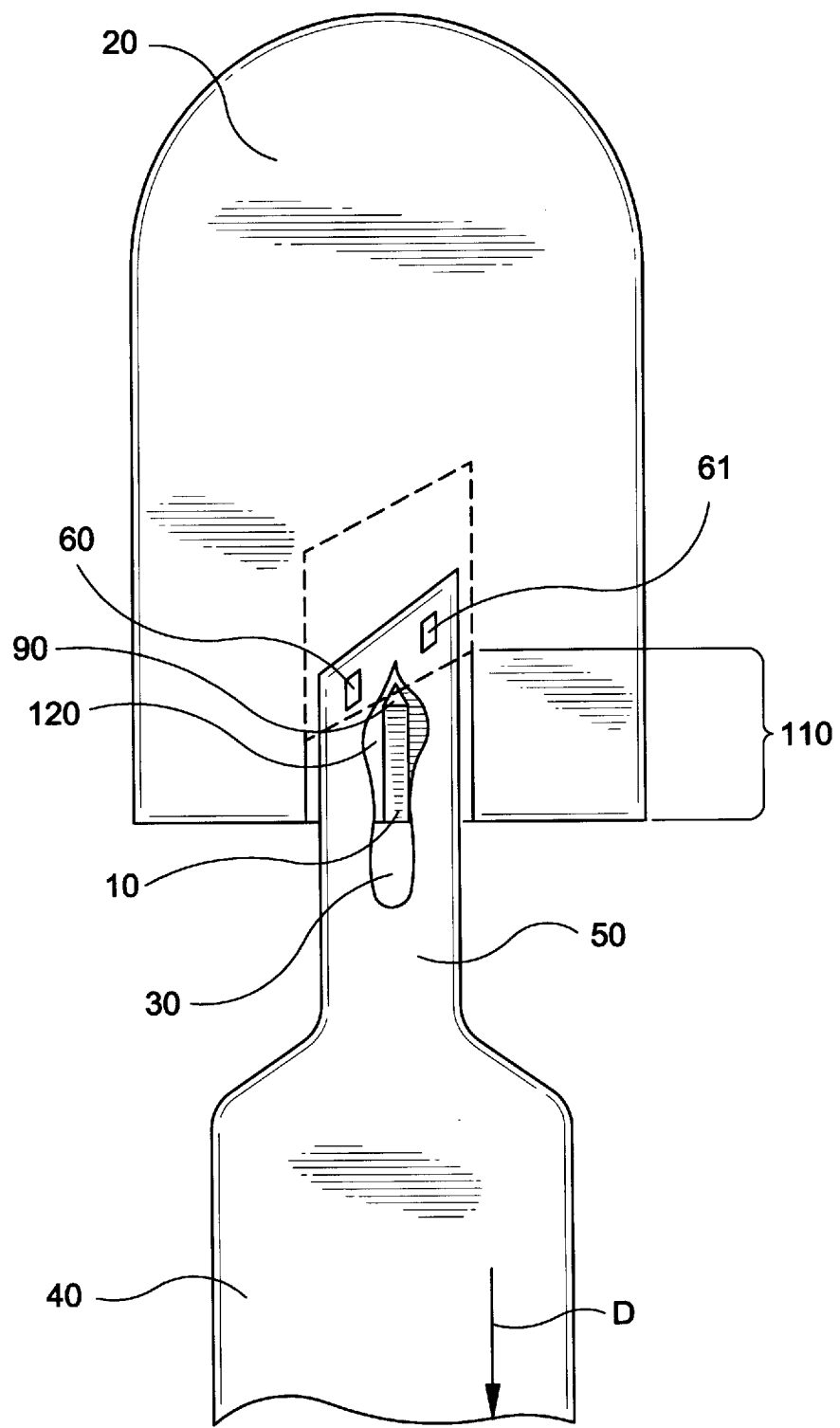
FIG. 6 is a top view of an iontophoretic system illustrating a fourth embodiment of the present invention.
Figure 7:
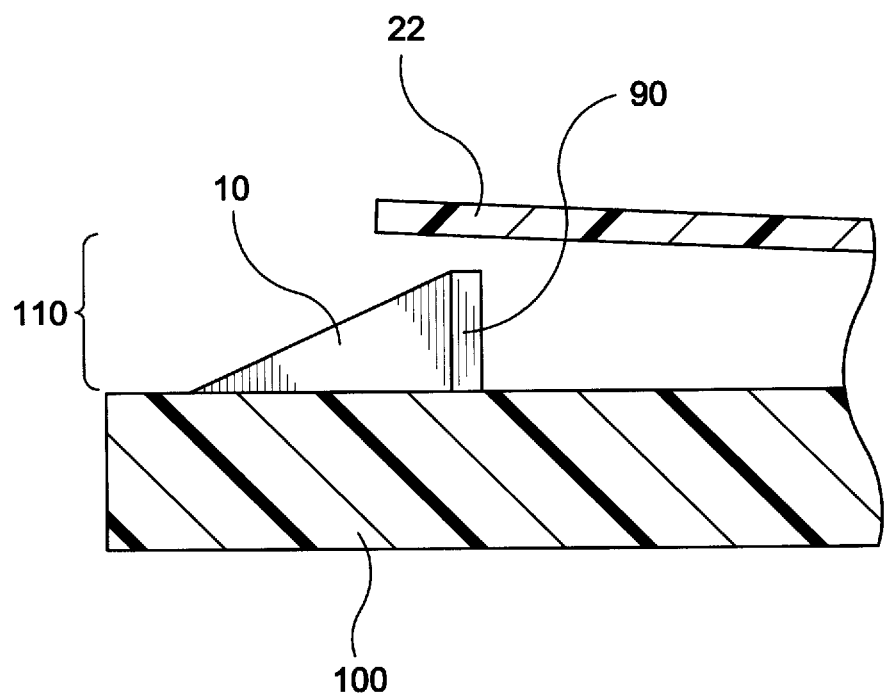
FIG. 7 is a sectional view of the controller of the fourth embodiment of the present invention.

In a fourth embodiment of the present invention, illustrated in FIGS. 6 and 7, a cutting edge 90 forms the rear edge of the lower protruding member 10. When the tab 50 is pulled out from the receiving portion 110 of the controller 20, the opening 30 of the tab 50 is, sliced open into at least two pieces, permanently disfiguring the tab. The cutting edge 90 may take any shape, but the sharper the edge, the less force will be required to remove and cut the patch. The cutting edge 90 may be located in any area of the receiving portion 110, so long as it causes the permanent disfigurement of the tab 50 when the tab 50 is removed.

In this embodiment, it is not necessary to squeeze the tab 50 inward to remove the tab. The user simply pulls on the patch 40 or tab 50 outwardly from the controller 20, causing the portion of the opening 30 nearest the electrical terminals 60 and 61 to contact the cutting edge 90. As more pulling force is applied, the cutting edge 90 begins to slice the tab 50 at the leading portion 120 of the opening 30. The cutting edge continues to slice the tab 50 until it is cut into two portions, from the front of the opening 30 to the end portion 45 of the tab 50. The tab 50, and thus the patch 40, is permanently disfigured and cannot be reinserted into the controller 20.

Moreover, the tab 50 may be designed so that when cutting edge slices through the tab it slices through one or more of the patch electrical connections, for example, connections 46 and 47. This last feature prevents an electrical connection between the patch and the controller even if an otherwise disfigured patch is forcibly reinserted back into the controller for attempted reuse. Without an electrical connection, no current can pass through the patch electrodes, and no iontophoresis can occur.

Thus, the present invention provides a new and useful iontophoretic system that (1) provides the user with tactile feedback and "snap" for respectively determining whether a patch is being properly inserted into and connected with a controller, (2) provides a secure a mechanical and electrical connection between the patch and the controller, and (3) prevents the reuse of previously-used patches by disfiguring them, in various ways, upon their removal from the controller.

Of course, it will be appreciated that the invention may take forms other than those specifically described, and the scope of the invention is to be determined solely by the following claims.

What is claimed is:

1. An iontophoretic system comprising:
    a current controller having an energy source, current regulation circuitry and a patch-receiving portion including an upper surface and a lower surface, and a first member protruding from said lower surface in a ramp-like fashion toward said upper surface and terminating in a top edge near said upper surface;
    a patch having an interconnection tab including an opening for engaging said first member when said interconnection tab is inserted into said patch-receiving portion of said current controller and said opening falls over said top edge of said first member;
    an active reservoir;
    a first electrode in the active reservoir;
    an electrical interconnector connecting the first electrode to current controller;
    a return reservoir;
    a second electrode in the return reservoir; and
    an electrical interconnector connecting the second electrode to the current controller.

2. The iontophoretic system according to claim 1, wherein said current controller further comprises a second member descending from said upper surface in a ramp-like fashion toward said lower surface and terminating in a bottom edge near said lower surface.

3. The iontophoretic system according to claim 1, wherein said current controller further comprises a plurality of second members, each second member descending from said upper surface in a ramp-like fashion toward said lower surface and terminating in a bottom edge near said lower surface, said second members located on each side of said first member.

4. The iontophoretic system according to claim 1, wherein said interconnection tab permanently deforms when a predetermined amount of force is applied to said interconnection tab to disengage said opening of said interconnection tab from said first member.

5. The iontophoretic system according to claim 1, wherein said first member of said current controller disfigures said interconnection tab of said patch upon removing said interconnection tab from said receiving portion.

6. The iontophoretic system according to claim 5, wherein the disfigurement of said interconnection tab comprises slicing through said opening of said interconnection tab.

7. The iontophoretic system according to claim 5, wherein said interconnection tab has a plurality of electrical connections to electrically connect said patch with said current controller, and the disfigurement of said interconnection tab comprises slicing through at least one of said electrical connections.

8. The iontophoretic system according to claim 1, wherein said first member of said current controller has a rear cutting edge.

9. A method for rendering an iontophoretic patch having an interconnection tab unreusable, said method comprising the steps of:
    inserting the interconnection tab into a patch-receiving portion of a current controller so an opening of the interconnection tab engages a member protruding from the patch-receiving portion of the current controller; and
    applying a predetermined amount of force to the sides of the interconnection tab to disengage the opening of the interconnection tab from the protruding member so as to permanently deform the interconnection tab.

10. A method for rendering an iontophoretic patch having an interconnection tab unreusable, said method comprising the steps of:
    inserting the interconnection tab into a patch-receiving portion of a current controller so an opening of the interconnection tab engages a member protruding from the patch-receiving portion of the current controller; and
    pulling the interconnection tab out from the patch-receiving portion so as to permanently disfigure the interconnection tab.

11. A method according to claim 10, wherein the protruding member has a rear cutting edge, and in the pulling step, the interconnection tab is pulled through the rear cutting edge.

* * * * *